United States Patent
Lopes Ferreira et al.

(10) Patent No.: US 8,518,679 B2
(45) Date of Patent: Aug. 27, 2013

(54) **COMPLEMENTATION OF THE *TRICHODERMA REESEI* SECRETOME LIMITING MICROBIOLOGICAL CONTAMINATIONS WITHIN THE CONTEXT OF INDUSTRIAL PROCESSES**

(75) Inventors: Nicolas Lopes Ferreira, Croisilles (FR); Antoine Margeot, Paris (FR)

(73) Assignee: IFP Energies Nouvelles, Rueil-Malmaison Cedex (FR)

( * ) Notice: Subject to any disclaimer, the term of this patent is extended or adjusted under 35 U.S.C. 154(b) by 364 days.

(21) Appl. No.: 12/809,271

(22) PCT Filed: Dec. 16, 2008

(86) PCT No.: PCT/FR2008/001743
§ 371 (c)(1),
(2), (4) Date: Sep. 27, 2010

(87) PCT Pub. No.: WO2009/106703
PCT Pub. Date: Sep. 3, 2009

(65) Prior Publication Data
US 2011/0008862 A1    Jan. 13, 2011

(30) Foreign Application Priority Data
Dec. 20, 2007 (FR) ................... 07 09120

(51) Int. Cl.
| | | |
|---|---|---|
| *C12P 7/10* | (2006.01) | |
| *C12N 9/00* | (2006.01) | |
| *C12N 9/42* | (2006.01) | |
| *C12N 1/20* | (2006.01) | |
| *C12N 15/00* | (2006.01) | |
| *C07H 21/04* | (2006.01) | |

(52) U.S. Cl.
USPC ........ 435/165; 435/186; 435/209; 435/252.3; 435/320.1; 536/23.2

(58) Field of Classification Search
None
See application file for complete search history.

(56) References Cited

U.S. PATENT DOCUMENTS
2006/0008885 A1    1/2006    Wahnon et al.
2009/0098624 A1    4/2009    Deinhammer et al.

FOREIGN PATENT DOCUMENTS
WO    WO 03/078644 A2    9/2003
WO    WO 2007/109750 A2    9/2007

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
International Search Report of PCT/FR2008/001743 (Dec. 7, 2009).
D. P. Bayrock et al., "Control of *Lactobacillus* Contaminants in Continuous Fuel Ethanol Fermentations by Constant or Pulsed Addition of Penicillin G," Applied Microbiology and Biotechnology, vol. 62, No. 5-6 (2003) pp. 498-502.
M. Baron et al., "Efficient Secretion of Human Lysozyme Fused to the Sh *ble* Phleomycin Resistance Protein by the Fungus *Tolypocladium geodes*," Journal of Biotechnology, vol. 24, No. 3 (1992) pp. 253-266.
A. Spencer et al., "Expression, Purification, and Characterization of the Recombinant Calcium-Binding Equine Lysozyme Secreted by the Filamentous Fungus *Aspergillus niger*: Comparisons with the Production of Hen and Human Lysozymes," Protein Expression and Purification, vol. 16, No. 1 (1999) pp. 171-180.

* cited by examiner

*Primary Examiner* — Christian Fronda
(74) *Attorney, Agent, or Firm* — Millen, White, Zelano & Branigan, P.C.

(57) ABSTRACT

The present invention describes the use of a genetically improved *Trichoderma reesei* strain allowing to limit microbiological contaminations during an industrial process. The genetic strain improvement allows the latter to overexpress an extracellular protein having known antimicrobial properties and compatible with the secretory system of strains of fungi such as *Trichoderma reesei*. This modified strain can be used to produce the cellulolytic and/or hemicellulolytic enzymes used in a method of producing ethanol from cellulosic or lignocellulosic materials referred to as "second generation" materials.

11 Claims, 1 Drawing Sheet

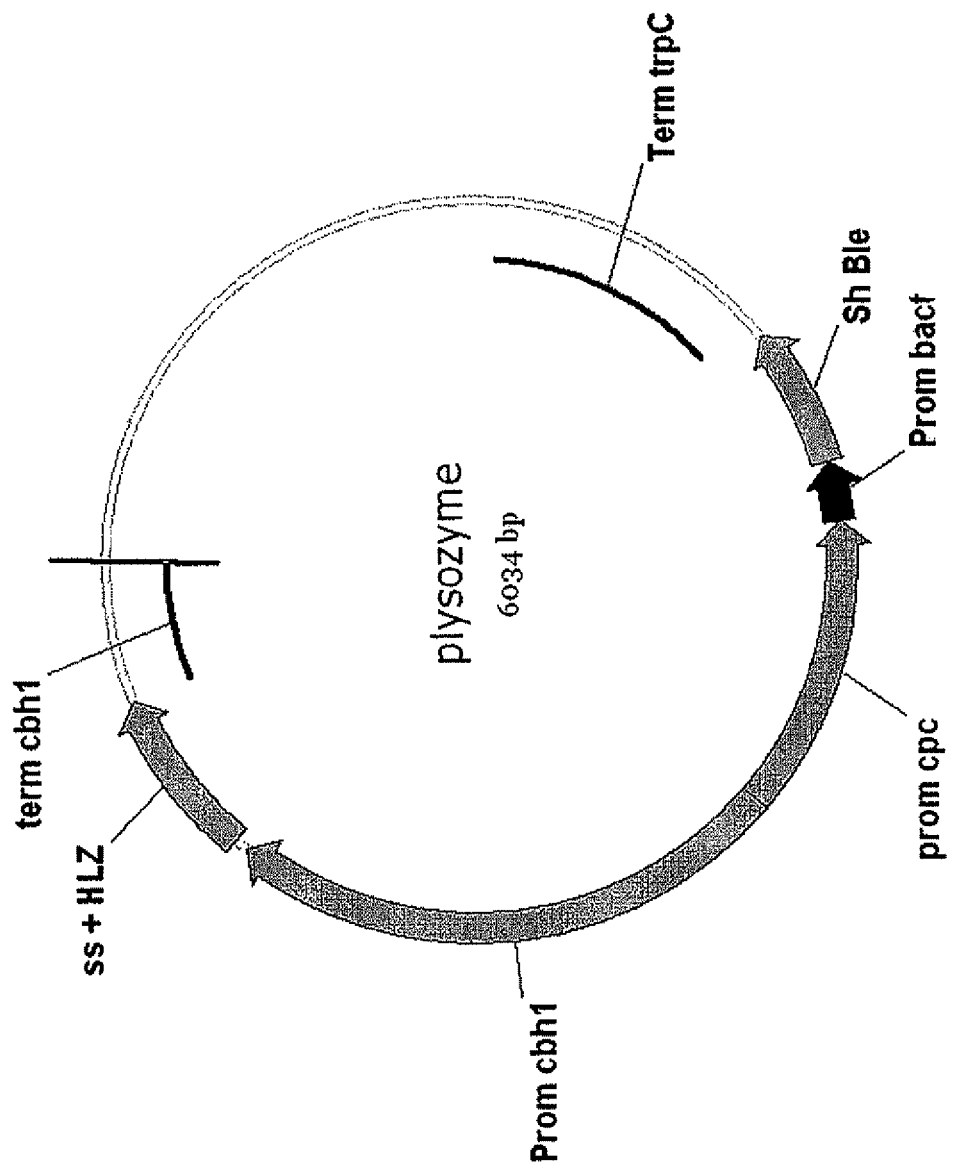

COMPLEMENTATION OF THE *TRICHODERMA REESEI* SECRETOME LIMITING MICROBIOLOGICAL CONTAMINATIONS WITHIN THE CONTEXT OF INDUSTRIAL PROCESSES

FIELD OF THE INVENTION

The present invention lies within the scope of a method referred to as "second generation" method of producing ethanol from lignocellulosic biomass, comprising stages of pretreatment of a cellulosic or lignocellulosic substrate, of enzymatic hydrolysis of the pretreated substrate and of alcoholic fermentation of the hydrolysate obtained.

BACKGROUND OF THE INVENTION

Lignocellulosic biomass represents one of the most abundant renewable resources on earth, and certainly one of the least expensive. The substrates considered are very varied since they concern both lignous substrates (broadleaved trees and coniferous trees), agricultural sub-products (straw) or sub-products from industries generating lignocellulosic waste (food-processing industries, paper industries).

Lignocellulosic biomass consists of three main polymers: cellulose (35 to 50%), hemicellulose (20 to 30%), which is a polysaccharide essentially consisting of pentoses and hexoses, and lignin (15 to 25%), which is a polymer of complex structure and high molecular weight, consisting of aromatic alcohols linked by ether bonds.

These various molecules are responsible for the intrinsic properties of the plant cell walls and they organize into a complex entanglement.

The cellulose and possibly the hemicelluloses are the targets of enzymatic hydrolysis, but they are not directly accessible to enzymes. These substrates therefore have to undergo a pretreatment prior to the enzymatic hydrolysis stage. The pretreatment aims to modify the physical and physico-chemical properties of the lignocellulosic material in order to improve the accessibility of the cellulose stuck in the lignin and hemicellulose matrix. It can also release the sugars contained in the hemicelluloses as monomers, essentially pentoses, such as xylose and arabinose, and hexoses, such as galactose, mannose and glucose.

Ideally, the pretreatment must be fast and efficient, with high substrate concentrations, and material losses should be minimal. There are many technologies available: acidic boiling, alkaline boiling, steam explosion (Pourquié J. and Vandecasteele J. P. (1993) Conversion de la biomasse lignocellulosique par hydrolyse enzymatique et fermentation. Biotechnologie, $4^{th}$ ed., René Scriban, coordinateur Lavoisier TEC & DOC, Paris, 677-700), Organosolv processes, or twin-screw technologies combining thermal, mechanical and chemical actions (Ogier J. C. et al. (1999) Production d'éthanol à partir de biomasse lignocellulosique, Oil & Gas Science & Technology 54:67-94). The pretreatment efficiency is measured by the hydrolysis susceptibility of the cellulosic residue and by the hemicellulose recovery rate. From an economic point of view, the pretreatment preferably leads to total hydrolysis of the hemicelluloses, so as to recover the pentoses and possibly to upgrade them separately from the cellulosic fraction. Acidic pretreatments under mild conditions and steam explosion are well suited techniques. They allow significant recovery of the sugars obtained from the hemicelluloses and good accessibility of the cellulose to hydrolysis.

The cellulosic residue obtained is hydrolyzed via the enzymatic process using cellulolytic and/or hemicellulolytic enzymes. Microorganisms such as fungi belonging to the *Trichoderma*, *Aspergillus*, *Penicillium* or *Schizophyllum* genera, or anaerobic bacteria belonging for example to the *Clostridium* genus, produce these enzymes containing notably cellulases and hemicellulases, suited for total hydrolysis of the cellulose and of the hemicelluloses.

Enzymatic hydrolysis is carried out under mild conditions (temperature of the order of 45-50° C. and pH value 4.8) and it is efficient. On the other hand, as regards the process, the cost of enzymes is still very high. Considerable work has therefore been conducted in order to reduce this cost: i) first, increase in the production of enzymes by selecting hyperproductive strains and by improving fermentation methods, then ii) decrease in the amount of enzymes in hydrolysis by optimizing the pretreatment stage or by improving the specific activity of these enzymes. During the last decade, the main work consisted in trying to understand the mechanisms of action of the cellulases and of expression of the enzymes so as to cause excretion of the enzymatic complex that is best suited for hydrolysis of the lignocellulosic substrates by modifying the strains with molecular biology tools.

Filamentous fungi, as cellulolytic organisms, are of great interest to industrialists because they have the capacity to produce extracellular enzymes in very large amounts. The most commonly used microorganism for cellulase production is the *Trichoderma reesei* fungus. Wild strains have the ability to produce, in the presence of an inductive substrate, cellulose for example, a secretome (all the proteins secreted) suited for cellulose hydrolysis. The enzymes of the enzymatic complex comprise three major types of activities: endoglucanases, exoglucanases and β-glucosidases. Other proteins having properties that are essential for the hydrolysis of lignocellulosic materials are also produced by *Trichoderma reesei*, xylanases for example. The presence of an inductive substrate is essential to the expression of cellulolytic and/or hemicellulolytic enzymes. The nature of the carbon-containing substrate has a strong influence on the composition of the enzymatic complex. It is the case of xylose which, associated with an inductive carbon-containing substrate such as cellulose or lactose, allows the activity referred to as xylanase activity to be significantly improved.

Conventional genetic techniques using mutagenesis have allowed cellulase-hyperproductive *Trichoderma reesei* strains such as MCG77 (Gallo—U.S. Pat. No. 4,275,167), MCG 80 (Allen, A. L. and Andreotti, R. E., Biotechnol-Bioengi 1982, 12, 451-459 1982), RUT C30 (Montenecourt, B. S. and Eveleigh, D. E., Appl. Environ. Microbiol. 1977, 34, 777-782) and CL847 (Durand et al., 1984, Proc. Colloque SFM "Génétique des microorganismes industriels". Paris. H. HESLOT Ed, pp 39-50) to be selected. The improvements have allowed to obtain hyperproductive strains that are less sensitive to catabolic repression on monomer sugars notably, glucose for example, in relation to wild strains.

The fact that genetic techniques intended to express heterologous genes within these fungic strains are now widely practised has also opened up the way for the use of such microorganisms as hosts for industrial production. New techniques of studying enzymatic profiles have made it possible to create very efficient host fungic strains for the production of recombining enzymes on the industrial scale [Nevalainen H. and Teo V. J. S. (2003) Enzyme production in industrial fungi-molecular genetic strategies for integrated strain improvement. In Applied Mycology and Biotechnology (Vol. 3) Fungal Genomics (Arora D. K. and Kchachatourians G. G. eds.), pp. 241-259, Elsevier Science]. One example of this type of modification is the production of cellulases from a *T. reesei* strain [Harkki A. et al. (1991) Genetic engineering of

*Trichoderma* to produce strains with novel cellulase profiles. Enzyme Microb. Technol. 13, 227-233; Karhunen T. et al. (1993) High-frequency one-step gene replacement in *Trichoderma reesei*. I. Endoglucanase I overproduction. Mol. Gen. Genet. 241, 515-522].

The sugars obtained by lignocellulosic biomass hydrolysis are pentoses (mainly xylose and arabinose), disaccharides (cellobiose) and glucose. The latter is readily converted to ethanol by the yeast *S. cerevisiae* used by all the alcoholic fermentation industries. Currently, no other microorganism reaches its performances on glucose under non-sterile conditions, i.e. a yield of the order of 0.47 g ethanol per gram of glucose, a productivity greater than or equal to 5 g/l×h, and final ethanol concentrations close to 10% by volume. *S. cerevisiae* affords many additional advantages resulting from many years of selection: resistance to ethanol, easy industrial implementation, etc. On the other hand, pentoses are rarely fermented by microorganisms, and when they are, the performances are poor. During the past years, considerable work has been done on the search for and/or the improvement of strains providing active fermentation of pentoses to ethanol. Four types of microorganisms have been studied: the yeasts fermenting pentoses naturally, recombined *S. cerevisiae* strains, thermophilic or mesophilic bacteria using pentoses.

Alcoholic fermentation under non-sterile conditions involves a high risk of contamination, of the fermenter by opportunistic microorganisms. The contamination sources can be of living or non-living nature. However, we shall only deal here with living contamination sources. These sources mainly include yeasts and bacteria. These microorganisms use the nutrients that are present, including the carbon source, and they are responsible for the formation of unwanted co-products such as lactic acid, acetic acid or even acetone and butanol. This kind of microorganisms is found wherever the conditions allow their growth, i.e. In the presence of a minimum amount of nutrients. It can be mentioned here that their nutritional requirements are: a source of carbon (generally sugars), a source of amino-acids (constituents of proteins), some vitamins and trace elements.

Furthermore, within the energetic raw materials considered, wheat straw for example, it is likely that microorganisms capable of contaminating the process can be found.

Thus, in the current and non-sterile method of producing second-generation ethanol, two stages are sensitive to a possible microbiological contamination: the enzymatic hydrolysis stage and the fermentation stage. The solutions currently known for fighting lactic contamination consist in lowering the pH value down to a value promoting the development of yeasts to the detriment of lactic bacteria. Yeasts are however less active at such acidic pH values. Another option consists in introducing bacterial contamination inhibitors, such as fluorine, antibiotics or sulfites, during the alcoholic fermentation stage. It is indeed during this stage of the method that the contaminant concentration is the highest. Using conventional antibacterial agents is relatively expensive and requires rather frequent fermentation process restarting procedures.

Limiting contamination risks potentially allows to save time and money for industrial processes of such scale and no solution should be neglected to overcome this problem.

Bacterial contamination is in fact a major problem in the production of ethanol by fermentation. Bacteria are naturally present within the production tool and they use the nutrients present in the medium, thus consequently competing with the yeasts used in the process. The growth and the viability of the yeast cells are therefore greatly affected by the presence of these bacteria and the final alcohol yield is also reduced thereby.

In general, lactic bacteria ferment sugars present in the fermentation musts and their growth is promoted by anaerobic conditions. They generally develop at a pH value of 5.5 but they can survive at a pH value as low as 3.0. These opportunistic bacteria can develop over a wide temperature range and they are tolerant to high alcohol concentrations in the medium. The presence of bacteria in second-generation ethanol production processes should be proscribed. Any improvement in the process leading to maximum limitation of this contamination has to be taken into consideration.

BRIEF DESCRIPTION OF THE FIGURES

FIG. 1 shows a diagrammatic map of a plasmid that can be used for the heterologous expression of the hlz gene by *T. reesei* under cellulase induction conditions.

SUMMARY OF THE INVENTION

The present invention describes a method of producing ethanol from lignocellulosic biomass, wherein the *Trichoderma reesei* genome is complemented by at least one enzyme likely to prevent microbiological contaminations.

DETAILED DESCRIPTION

In the method of producing second-generation ethanol described in the present invention, in order to prevent microbiological contaminations, a genetically engineered fungic strain belonging to the *Trichoderma* genus and overexpressing, by means of genetic techniques known to the person skilled in the art, at least one extracellular protein having antimicrobial properties is used to produce cellulolytic and/or hemicellulolytic enzymes.

The fungic strain (cellulolytic microorganism) preferably belongs to the *Trichoderma reesei* species.

Using a protein with antimicrobial properties allows to ensure protection against a wide range of Gram-positive bacteria, notably against lactic bacteria. These bacteria develop in second-generation ethanol production processes as early as the enzymatic hydrolysis stage and mainly upon alcoholic fermentation since the temperature during this stage is of the order of 30° C. to 35° C.

Furthermore, complementing the *Trichoderma reesei* genome directly by at least one enzyme having the desired bactericidal properties allows to avoid introducing an exterior bactericidal agent into the ethanol production process, this strain being already the one used for enzymatic hydrolysis.

Non-exclusive examples of enzymes having an antimicrobial activity are lysozyme, pyocyanase or lactose peroxydase.

More preferably, the extracellular protein used for complementing the *Trichoderma reesei* genome is human or chicken lysozyme.

Lysozyme is a hydrolase type enzyme (acidic and secreted by leucocytes) discovered by Alexander Fleming in 1922. It is a globular protein consisting of 129 amino-acids that are found in a certain number of secretions (tears, saliva, etc.). It can also be extracted from egg white, which characterizes its use in oenology. Used for several years in the pharmaceutical and food-processing industries, it has been recently added in some oenology processes (wine maturation for example) in order to control contamination by lactic bacteria. This enzyme acts by degrading their wall (hydrolyzes the covalent bonds between N-acetylmuramic acid and the fourth carbon atom of N-acetylglucosamine). From a biochemical point of view, lysozyme has an optimum activity between 40° C. and 45° C., which is entirely compatible with the temperatures used for enzymatic hydrolysis, and it can remain active up to 62° C. As regards the optimum pH value, the enzymatic activity of this protein is not or little disturbed within a pH value range between 3.5 and 7, but it can however remain active between 2 and 10.

Lysozyme is also used as a preservative in many food products likely to contain lactic bacteria such as cheese, tofu or sake. The use of lysozyme in brewing processes has recently won attention and there are many applications in the brewing stages. Lysozyme is efficient against all lactic bacteria. Furthermore, Gram-negative bacteria and yeast are not attacked by this antimicrobial agent.

Lysozyme also affords the advantage of limiting the use of $SO_2$, a product that is very often used today to limit microbiological contaminations in industrial processes, but that is expensive. Lysozyme can also play a protective role in case of difficult fermentation ends. In fact, nitrogen deficiencies make alcoholic fermentation ends difficult, with a risk of development of lactic bacteria that degrade the oses not yet fermented. Addition of lysozyme allows to prevent or to deal with this type of problem with a high efficiency.

In the case of biological production of ethanol according to the present invention, the main advantage lies in the fact that lysozyme is a protein that can be directly expressed by *Trichoderma reesei*.

The heterologous expression of human lysozyme has been developed in the filamentous fungus *Tolypocladium geodes* (Michel Baron, "Optimisation au niveau moléculaire de souches transformées de *Tolypocladium geodes* pour la sécrétion de deux protéines humaines d'intérêt thérapeutique>> (1991), Ph.D. thesis, Paul Sabatier University).

With a view to complementation of the genome of *T. reesei* by the hlz gene expressing the lysozyme, a model plasmid construction is achieved using the conventional molecular biology methods known to the person skilled in the art. The genetic construction to be integrated in the genome of *T. reesei* comprises the coding sequence of human lysozyme inserted between the elements allowing its expression and its secretion among fungi. Within the context of a joint cellulase production, the nucleotide sequences must allow heterologous expression of the hlz gene. The promoter, the signal sequence and the terminator surrounding this gene must therefore comprise one or more motifs known to the person skilled in the art as being involved in the specific induction of these enzymes. In particular, the fungic promoter used can be selected, in a non-exclusive manner, from among the following: gpd (*A. nidulans*), cbh1, egl1, egl2, xyn1. The fungic signal sequence can for example be selected from among cbh1, egl1, egl2, xyn1. A fusion of lysozyme with an export-facilitating protein (Sh-Ble for example), as described in M. Baron's Ph.D. thesis, can be used. The fungic terminator can be of any nature, cbh1 or TrpC (*A. nidulans*) for example.

Construction must finally allow to identify the strain that has integrated this lysozyme gene. Several genes conferring resistance to an antibiotic (phleomycin, hygromycin, etc.) or allowing auxotrophic screening (gene amdS for acetamide) are known to the person skilled in the art and they can therefore be used for industrial *T. reesei* strains.

An example of plasmid construction allowing said expression is described in FIG. 1. In this FIGURE, the captions used are as follows: "Prom" for promoter, "Term" for terminator, "bact" for bacteria, "ss+HLZ" for lysozyme coding gene with functional addressing sequence for *T. reesei*, "Sh-Ble" for gene conferring resistance to the phleomycin antibiotic.

The construction thus achieved allows the selection of a transformant by an incorporation is then incorporated in the genome of the fungic strain already used to produce cellulases, for example the hyperproducing strain CL847 (Durand at al., 1984), according to methods already described and known to the person skilled in the art, for example described by Penttila at al. (1987).

The transformants obtained are selected for a high lysozyme activity, according to the method described above by M. Baron (1991, Ph.D. thesis, Paul Sabatier University, Toulouse).

The strain selected secretes, in addition to cellulolytic enzymes, a proportion of lysozyme between 1% and 5% of the proteic secretions of the strain which, within the context of a typical enzymatic hydrolysis, carried out for example with 20 mg/g substrate and 20% dry matter, allows to be in a lysozyme concentration range in the hydrolysis reaction between 40 and 200 mg/l, these proportions being commonly used in the industry to prevent lactic bacteria contaminations.

The enzymes are then produced according to a conventional process of any nature. The enzymes are separated and used for the hydrolysis reaction as described above. No other precaution is required to prevent bacterial contaminations for the rest of the process, contrary to what has to be done with a conventional strain.

The action of the bactericidal agent is all the more efficient as the lactic bacteria concentration in the medium is low. In the method according to the present invention, the bactericidal agent is produced by the microorganism used for secretion of the enzymes employed during the enzymatic hydrolysis stage. Now, at this stage of the process, owing notably to the operating temperature conditions, lactic proliferation remains little probable or limited in comparison to the one that can take place during the subsequent alcoholic fermentation stage.

The cellulosic or lignocellulosic materials used in the method according to the present invention are selected from among straws, wood, forest crops, alcohol-producing crop, sugar crop and cereal crop residues, paper industry residues, cellulosic and lignocellulosic material transformation products.

The material to be hydrolyzed is suspended in the aqueous phase in a proportion of 6% to 25% dry matter, preferably 10% to 20%, the pH value is adjusted between 4 and 5.5 (preferably between 4.5 and 5.2) and the temperature between 40° C. and 60° C. (preferably between 45° C. and 50° C.). The hydrolysis reaction generally lasts from 15 to 48 hours depending on the efficiency of the pretreatment applied, on the composition of the enzymatic cocktail and on the amount of enzymes added. The reaction is monitored by titrating the sugars released. The sugar solution obtained is then separated from the non-hydrolyzed fraction by filtration or centrifugation, then it is used for ethanolic fermentation. The ethanolic fermentation stage is carried out according to the general knowledge of the person skilled in the art, in the presence of yeasts such as, for example, *Saccharomyces cerevisiae* or *Zymomonas mobilis*, the optimum fermentation temperature generally ranging between 30° C. and 35° C.

According to the present invention, using, in order to produce cellulolytic and/or hemicellulolytic enzymes, a genetically engineered *Trichoderma reesei* strain overexpressing at least one extracellular protein having antimicrobial properties can be performed in a process wherein the enzymatic hydrolysis stage is distinct from the fermentation stage.

According to another embodiment, the method according to the present invention is a SSF (simultaneous saccharification and fermentation) process that consists in carrying out enzymatic hydrolysis and alcoholic fermentation in a single stage. In this case, the operating temperature is relatively low (about 34° C.) and therefore more conducive to bacterial contamination.

The invention claimed is:

1. A method of producing ethanol from cellulosic or lignocellulosic materials, comprising treating a cellulosic or lignocellulosic substrate with a genetically engineered fungal strain belonging to the *Trichoderma* genus over-expressing lysozyme comprising antimicrobial properties, wherein said treatment step is conducted prior to or simultaneously with the steps of enzymatic hydrolysis of the substrate and alcoholic fermentation of the thus-obtained hydrolysate.

2. A method of claim 1, wherein the fungal strain belongs to the *Trichoderma reesei* species.

3. A method of claim 1, wherein the cellulosic or lignocellulosic material selected from the group consisting of
   straw;
   wood;
   a forest crop selected from the group consisting of forest crop, alcohol-producing crop, sugar crop or cereal crop residues;
   paper industry residues; and
   a cellulosic or a lignocellulosic material transformation product.

4. A method of claim 1, wherein the enzymatic hydrolysis step is carried out at a temperature ranging between 40° C. and 60° C. and at a pH value ranging between 4 and 5.5.

5. A method of claim 1, wherein the enzymatic hydrolysis step is followed by an ethanolic fermentation step.

6. A method of claim 1, wherein the enzymatic hydrolysis step and the ethanolic fermentation step are carried out simultaneously.

7. A method of claim 1, wherein the genetically engineered fungal strain additionally produces a cellulolytic or a hemicellulolytic enzyme.

8. A method claim 1, wherein the lysozyme is a heterologous protein genetically engineered to be overproduced in anti-microbially effective amounts.

9. A method of claim 1, wherein the lysozyme is effective to prevent contamination of the substrate or the hydrolysate with Gram-positive bacteria.

10. A method of claim 9, wherein the Gram-positive bacteria are lactic bacteria.

11. A method of claim 1, wherein the lysozyme comprises at least 1% of the protein secreted by the fungal strain.

* * * * *

UNITED STATES PATENT AND TRADEMARK OFFICE
CERTIFICATE OF CORRECTION

PATENT NO.        : 8,518,679 B2
APPLICATION NO. : 12/809271
DATED             : August 27, 2013
INVENTOR(S)       : Lopes Ferreira et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 462 days.

Signed and Sealed this

Fifteenth Day of September, 2015

Michelle K. Lee
*Director of the United States Patent and Trademark Office*